United States Patent
Marell et al.

(10) Patent No.: US 11,067,387 B2
(45) Date of Patent: Jul. 20, 2021

(54) ADAPTIVE INSTRUMENT KINEMATIC MODEL OPTIMIZATION FOR OPTICAL SHAPE SENSED INSTRUMENTS

(71) Applicant: KONINKLIJKE PHILIPS N.V., Eindhoven (NL)

(72) Inventors: Milan Jan Henri Marell, Noord-Brabant (NL); Femke Van Belzen, Eindhoven (NL); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 674 days.

(21) Appl. No.: 15/117,496

(22) PCT Filed: Feb. 9, 2015

(86) PCT No.: PCT/IB2015/050952
§ 371 (c)(1),
(2) Date: Aug. 9, 2016

(87) PCT Pub. No.: WO2015/128761
PCT Pub. Date: Sep. 3, 2015

(65) Prior Publication Data
US 2016/0349044 A1 Dec. 1, 2016

Related U.S. Application Data
(60) Provisional application No. 61/945,927, filed on Feb. 28, 2014.

(51) Int. Cl.
*G01B 11/24* (2006.01)
*A61B 34/20* (2016.01)
(Continued)

(52) U.S. Cl.
CPC .............. *G01B 11/24* (2013.01); *A61B 34/20* (2016.02); *G01B 11/18* (2013.01); *G01B 21/045* (2013.01);
(Continued)

(58) Field of Classification Search
CPC ...... G01B 11/24; G01B 11/18; G01B 21/045; A61B 34/20; A61B 2034/102; A61B 2034/2061; A61B 2017/00725
(Continued)

(56) References Cited

U.S. PATENT DOCUMENTS 8,358,883 B2    1/2013  Prisco
8,460,236 B2    6/2013  Roelle et al.
(Continued)

OTHER PUBLICATIONS

Kiruluta et al., Predictive Head Movement Tracking Using a Kalman Filter, IEEE Transactions on Systems, Man, and Cybernetics—Part B: Cybernetics, vol. 27, No. 2 (Year: 1997).*
(Continued)

*Primary Examiner* — Toan M Le
*Assistant Examiner* — Xiuqin Sun (57) ABSTRACT

A shape sensing system comprises a processor coupled to a memory storage device and a predictive model module stored in the memory storage device and configured to receive shape sensing measurements and predict next shape sensing measurements based upon current state data for a shape sensing enabled device, the predictive model module including a Kalman filter and at least one reference model employed by the Kalman filter. The Kalman filter employs the reference model(s) and the current state data to predict new shape data by weighting the reference model(s) versus the current state data to improve shape data measurements.

13 Claims, 5 Drawing Sheets

(51) Int. Cl.
  *G01B 11/16*   (2006.01)
  *G01B 21/04*   (2006.01)
  *A61B 17/00*   (2006.01)
  *A61B 34/10*   (2016.01)

(52) U.S. Cl.
  CPC ............... *A61B 2017/00725* (2013.01); *A61B 2034/102* (2016.02); *A61B 2034/2061* (2016.02)

(58) Field of Classification Search
  USPC ........................................................ 702/167
  See application file for complete search history.

(56) References Cited

U.S. PATENT DOCUMENTS

| | | | | |
|---|---|---|---|---|
| 8,996,094 | B2* | 3/2015 | Schouenborg | A61B 10/02 |
| | | | | 600/426 |
| 2005/0165292 | A1* | 7/2005 | Simon | A61B 6/481 |
| | | | | 600/407 |
| 2010/0030063 | A1* | 2/2010 | Lee | A61B 5/06 |
| | | | | 600/424 |
| 2011/0109898 | A1* | 5/2011 | Froggatt | G01M 11/025 |
| | | | | 356/73.1 |
| 2012/0271339 | A1* | 10/2012 | O'Beirne | A61M 25/104 |
| | | | | 606/194 |
| 2013/0190726 | A1* | 7/2013 | Kesner | A61M 25/0116 |
| | | | | 604/510 |
| 2013/0204124 | A1 | 8/2013 | Duindam et al. | |
| 2014/0219531 | A1* | 8/2014 | Epstein | G01R 33/56308 |
| | | | | 382/131 |
| 2014/0276937 | A1* | 9/2014 | Wong | A61B 34/30 |
| | | | | 606/130 |
| 2014/0311113 | A1* | 10/2014 | Bonefas | A01D 34/001 |
| | | | | 56/10.2 R |

OTHER PUBLICATIONS

Gherlone, M. et al., "Shape sensing of 3D frame structures using an inverse Finite Element Methos", Int. Journal of Solids and Structures, 49 (2012) 3100-3112.

* cited by examiner

ADAPTIVE INSTRUMENT KINEMATIC MODEL OPTIMIZATION FOR OPTICAL SHAPE SENSED INSTRUMENTS

CROSS-REFERENCE TO PRIOR APPLICATIONS

This application is the U.S. National Phase application under 35 U.S.C. § 371 of International Application Serial No. PCT/IB2015/050952, filed on Feb. 9, 2015, which claims the benefit of U.S. Application Ser. No. 61/945,927, filed on Feb. 28, 2014. These applications are hereby incorporated by reference herein.

BACKGROUND

Technical Field

This disclosure relates to medical instruments and more particularly modeling of instruments equipped with optical shape sensing for medical and mechanical applications.

Description of the Related Art

In many minimally invasive healthcare procedures, it is advantageous to track medical devices such as guide wires and catheters. Optical shape sensing enables this by measuring and analyzing the light reflected from all positions of a multi-core optical fiber built into an elongated medical device. When interferometry is used, a full distribution of strain of every individual core along the fiber is obtained, which can be converted into shape. Optical shape sensing is sensitive to noise in the shape sensing measurements and can cause the system to reconstruct erroneous (unphysical) shapes. Changes in temperature or pressure do not, in general, significantly affect shape sensing. However, movement or vibrations occurring on a timescale similar to the time of a shape sensing measurement can produce erroneous shapes.

SUMMARY

In accordance with the present principles, a shape sensing system includes a processor coupled to a memory storage device. A predictive model module is stored in the memory storage device and is configured to receive shape sensing measurements and predict next shape sensing measurements based upon current state data for a shape sensing enabled device. The predictive model module includes a Kalman filter and a reference model. The Kalman filter employs the at least one reference model and the current state data to predict new shape data by weighting the at least one reference model versus the current state data to improve shape data measurements.

Another shape sensing system includes a processor and memory coupled to the processor. A prediction module is stored in the memory and configured to receive shape sensing measurements from an optical shape sensing enabled device and predict kinematics of the optical shape sensing enabled device. The prediction module includes a Kalman filter and a reference model of mechanical properties of the shape sensing enabled device. The Kalman filter is configured to employ the model to determine predicted states of the shape sensing enabled device based on a current state of the shape sensing enabled device. A model parameter adaption module is configured to update the reference model in accordance with adaptation data.

A method for sensing a shape of an instrument includes obtaining measured shape data from a shape sensing enabled device; obtaining model data from a dynamic model of the shape sensing enabled device; inputting the measured shape data and the model data to a Kalman filter; and computing a weighted average between the measured shape data and the model data to predict new state data to improve the measured shape data.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and methods are provided that employ mechanical or other properties of a shape sensing enabled device to predict a future shape or shapes of the shape sensing enabled device and to correct for any kinematic inconsistencies. In particular, an adaptive kinematic model is employed to capture spatio-temporal behavior of the shape sensing enabled device whose model parameters may be learned from a library of previously acquired training cases and may be adaptively tuned to optimize tracking performance at different phases during an interventional procedure. Machine learning is not required, however may be employed in some embodiments. Mechanical/kinematic properties of some medical devices can be measured directly or can follow directly from material parameters.

A shape-sensed instrument may, for example, be described by a linear time invariant model or with an adaptive non-linear model that is locally linearized around a system operating point at any given moment during a procedure. This model can have mechanical parameters that capture the behavior of any elongated flexible medical device including catheters, guidewires, sheaths, endoscopes, etc. or any combination of such instruments with other devices, e.g., a secondary device in a working channel of an endoscope.

The stability and accuracy of reconstructed shapes is improved in accordance with the present principles. The present approach uses a dynamic model (e.g., physical laws of motion) of the system, known control inputs to that system, and measurements (such as from sensors) to form an estimate of the system's spatio-temporally-varying quantities (its state) that is better than the estimate obtained by using any one measurement alone.

A kinematic model used in combination with measurement data is referred to as Kalman filtering. A Kalman filter accepts measurement data and uses this 'state' data and the kinematic model of the device to calculate a new shape of the device. A measured state and predicted state (from models) are combined as a weighted average to improve the measurement accuracy. The Kalman filter may also provide confidence scores or information. Other filters may be employed to remove erroneous shape data based on the confidence or other criteria, for example. All data can be employed to predict the new shape of the medical instrument based on its kinematic model.

The kinematic model is used for the computation of time evolving behavior of an optical shape sensing (OSS) enabled device. The Kalman filter may include a sensor fusion algorithm that balances noisy measurements being acquired against prior knowledge about a discrete-time system that is described mathematically in state evolution equations. One example of the state equations may include the form, e.g., $x_k = f(x_{k-1}, v_{k-1}, w_{k-1})$, $z_k = g(x_k, v_k)$ where $x \in R^n$ is the state of the system, $u \in R^l$ is the input, $z \in R^m$ is the measurement, k is an index and w, v are the process and measurement noise, respectively.

Measurements taken by a shape sensing system may be corrupted by noise and any distortions arising from the acquisition process (e.g., blurring, etc.). The origin of these artifacts is usually two-fold. Part of the artifact originates from the measurement system itself, the other part has an external source. Measurement artifacts can negatively influence the algorithm used for the reconstruction of the shape of an optical fiber. The visible effects range from slight uttering of the shape to a complete failure of the shape reconstruction.

In accordance with the present principles, stability and accuracy of the reconstructed shapes are improved by model-based processing methods. One such model-based method may include, e.g., a Kalman filter. Such a filter reduces the noise on the calculated shape of the fiber and its apparent motion by comparing the measurement data to a dynamic model of the shape enabled device (e.g., a catheter, etc.) supporting a measurement fiber(s), thereby stabilizing the reconstructed shape improving the location accuracy and reducing unphysical movement.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc. The processor may include any computer processing unit or microprocessor (e.g., general purpose graphical processing units (GP-GPUs), etc.).

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes, which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
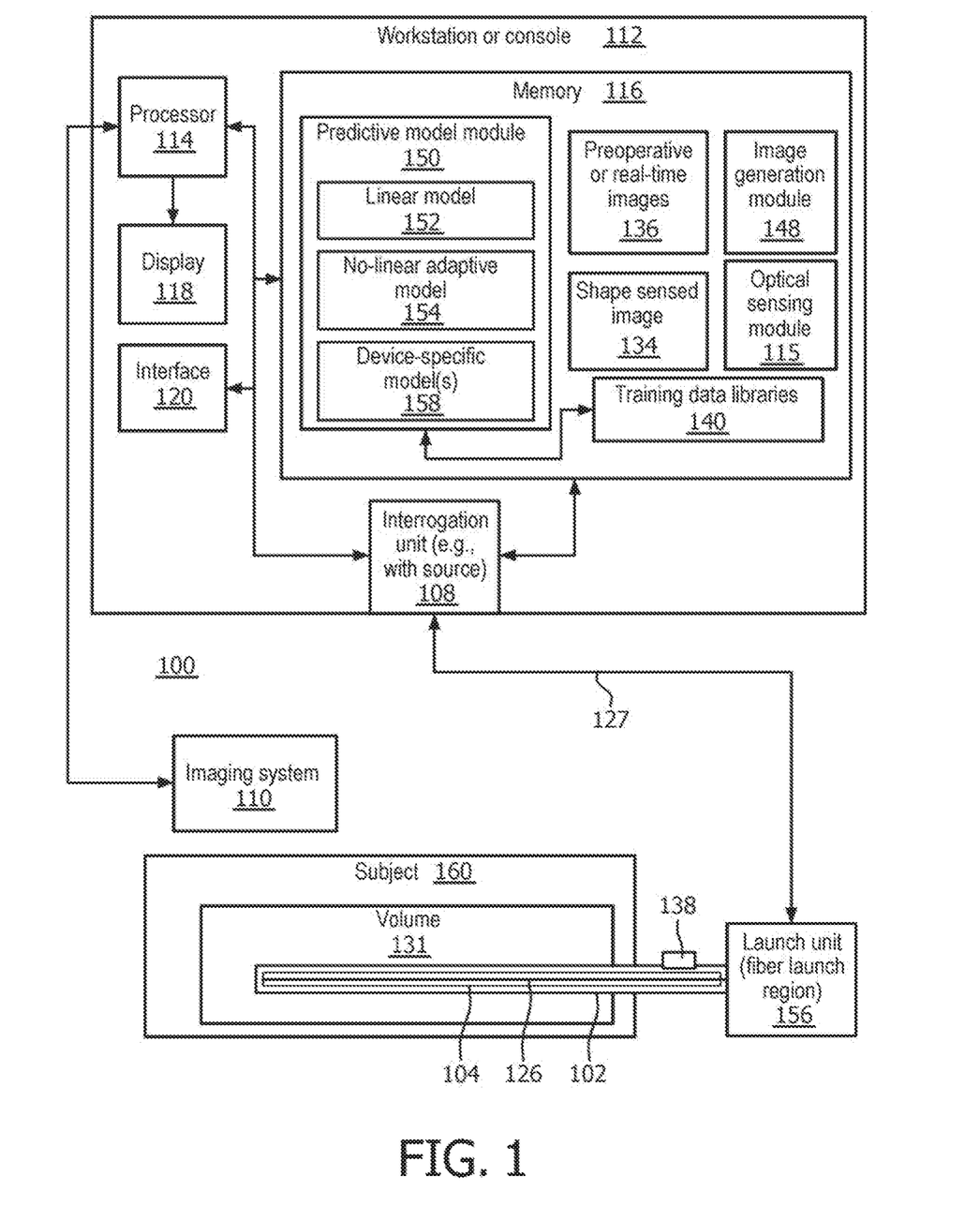
FIG. 1 is a block/flow diagram showing a shape sensing system, which employs a prediction module for improving accuracy and stability of shape data in accordance with one embodiment.

Referring now to the drawings in which like numerals represent the same or similar elements and initially to FIG. 1, a system 100 for reconstruction and prediction of shape data for shape sensing enabled devices is illustratively shown in accordance with one embodiment. System 100 may be employed in any mechanical or medical applications, e.g., any intravascular, endoluminal, orthopaedic, surgical, minimally-invasive intervention, etc. employing the use of shape sensing for instrument shape and position tracking.

System 100 may include a workstation or console 112 from which a procedure is supervised and/or managed. Workstation 112 preferably includes one or more processors 114 and memory 116 (memory storage device) for storing programs and applications. Memory 116 may store an optical sensing module 115 configured to interpret optical feedback signals from a shape sensing device 104. Optical sensing module 115 is configured to use the optical signal feedback (and any other feedback, e.g., electromagnetic (EM) tracking) to reconstruct deformations, deflections and other changes associated with a medical or shape sensed instrument 102 and/or its surrounding region. The instrument 102 may include a catheter, a guidewire, a probe, an endoscope, a robot, an electrode, a filter device, a balloon device, or other medical component, etc.

The shape sensing device 104 on instrument 102 includes one or more optical fibers (or optical fiber cores or channels) 126, which are coupled to the instrument 102 in a set pattern or patterns. The optical fibers or cores 126 and/or instrument 102 connect to the workstation 112 through cabling 127. The cabling 127 and other patch cords, etc. may include fiber optics, electrical connections, other instrumentation, etc., as needed. Shape sensing device 104 may be based on fiber optic Bragg grating sensors. A fiber optic Bragg grating (FBG) may include discrete elements (e.g., a short segment of optical fiber that reflects particular wavelengths of light and transmits all others) or can be continuously distributed along an entire fiber length. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used to increase reflection along optical fiber. The reflected light is read interferometrically so that strain changes can be detected.

Strain sensing is performed over the length of a fiber. Incorporating multiple cores, e.g., four or more cores, embedded in a shape sensing enabled structure permits a three dimensional form of such a structure to be precisely determined, typically with better than 1 mm accuracy. For reconstruction of a 3D shape, a central core with at least three cores wound around the central core in a helical fashion may be employed. Along the length of the fiber, at various positions, a multitude of FBG sensors can be located (e.g., 4 or more fiber sensing cores). Strain is sensed along the whole fiber length so that the curvature or shape of the structure can be inferred as a function of position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In one embodiment, workstation 112 includes an image generation module 148 configured to receive feedback from the shape sensing device 104 and render position data. The image generation module 148 renders the information about the position of the device 104, and can also combine the position information with imaging data of a patient anatomy. This may include either live data from an imaging system 110, or data that was acquired pre-operatively, such as by employing magnetic resonance (MR), computed tomography (CT), etc.

An image or images 134 of the shape sensing device 104 within a space or volume 131 can be displayed on a display device 118. Workstation 112 includes the display 118 for viewing internal images of a volume 131 in a subject (e.g., a patient) 160 or and may include the image 134 as an overlay or other rendering of the sensing device 104 with pre-operative or intra-operative (real-time) images 136. An imaging system 110 may be provided for intra-operative imaging (or pre-operative imaging). The imaging system 110 may include, e.g., an ultrasound system, a fluoroscopy system, etc. Display 118 may also permit a user to interact with the workstation 112 and its components and functions, or any other element within the system 100. This is further facilitated by an interface 120, which may include a keyboard, mouse, a joystick, a haptic device, or any other peripheral or control to permit user feedback from and interaction with the workstation 112.

A launch unit 156 provides a launch region for the shape sensing device 104. The shape sensing device 104 is coupled through the launch region to an interrogation module 108 having a light source(s) for sensing or probing the shape sensing device 104. In accordance with the present principles, refinement of the shape-sensed position data may be provided by weighting measured data with model data by, e.g., Kalman filtering. In one particularly useful embodiment, erroneous data can be determined by predictive modeling of the shape sensing enabled instrument 102. The shape sensing enabled instrument 102 may be modeled using a predictive model module (prediction module) 150. The prediction module 150 includes dynamic models of shape sensing enabled instruments 102, which can be employed to predict the behavior of the instruments 102. In one embodiment, the dynamic models may include, e.g., a linear time-invariant model 152 with an adaptive non-linear model 154 that is locally linearized around a system operating point at any given moment during a procedure. The models 152, 154 may include noise models, kinematic models, finite elements models, analytical models (mathematical equations to describe motion), etc. The model or models can have mechanical parameters that capture the behavior of any elongated flexible medical instrument (102) including catheters, guidewires, sheaths, endoscopes, or any combination of such instruments with other devices, e.g., a secondary device in the working channel of a miniature endoscope.

The dynamic models in module 150 for the shape sensing enabled instrument 102 are derived beforehand, by measuring mechanical and materials properties of the shape sensing enabled instrument 102. This may be performed by mounting the shape sensing enabled instrument 102 to an apparatus that moves the instrument 102 through a set of canonical shapes that serve as a reference or "ground-truth" to which the model parameters are adaptively tuned to make the optical shape sensing (OSS) measured shape match a reference as closely as possible. The measurements that are recorded are employed to determine the dynamic model of the instrument 102 via system identification methods.

The dynamic models of module 150 may include employing material parameters (stiffness, material density, geometry, etc.) of a medical device family (e.g., a series of catheters) to perform a forward prediction of the shape and velocity. The dynamic models of module 150 can also employ input from other imaging modalities 110 to continuously adjust medical device model parameters, to improve the accuracy (in real-time). This is described with reference to FIG. 3.

Memory 116 may be configured to store device-specific model data 158 in the predictive model 150. In one embodiment, the instrument 102 may include memory 138, for example, a read-only (ROM) chip built into a connector of the instrument 102, thereby allowing the read-out system to immediately adjust the reconstruction/filtering to the connected instrument 102. This may be to identify the instrument, identify the appropriate model to be used, provide filter parameters associated with the instrument 102, etc.

A library or libraries 140 of training datasets capturing both the "ground-truth" reference motion and OSS-measured motion of tracked instruments of the same type may be included in the predictive model module 150 or separately stored. These libraries 140 can be derived from an apparatus to move a shape-sensed instrument 102 through a set of canonical shapes or from clinical use cases by physicians who use/test the instrumentation in training mode. These libraries 140 can be adaptively tuned to optimize tracking performance at different phases or under different conditions during an interventional procedure.

In these cases, the reference motions can be captured from imaging data (from imaging system 110), electromagnetic tracker based measurements, optical camera based measurements, or similar sensing measurements, which allow for device location and shape to be determined independently of OSS.

Figure 2:
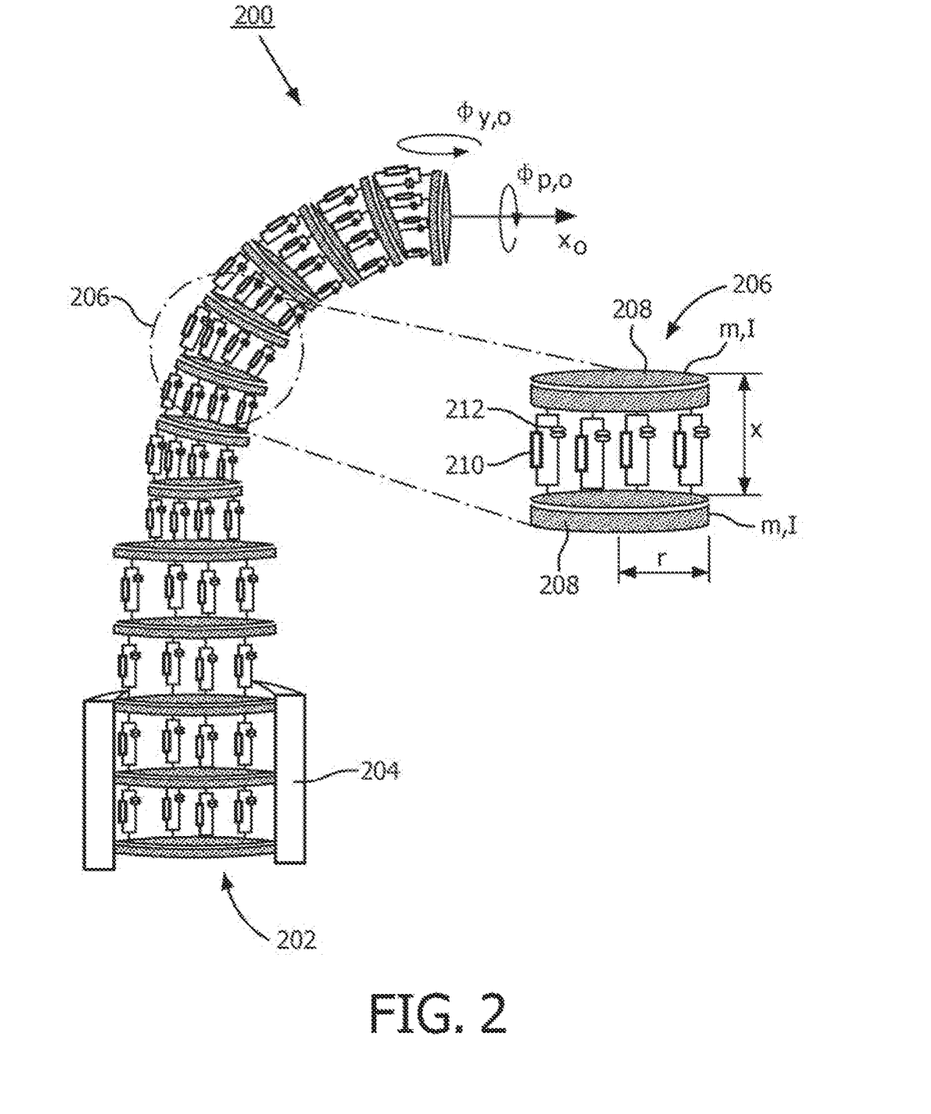
FIG. 2 is a perspective view showing a kinematic model of a catheter and sheath over a portion of the catheter in accordance with one embodiment.

Referring to FIG. 2, an example of a mechanical model 200 of a catheter 202 having a support tube 204 thereon is illustratively shown. In this illustrative example, the catheter 202 and the support tube or sheath 204 (which stiffens a portion of the catheter 202) are modeled as spring-damper elements 206 between plates 208. The plates 208 include a mass m and a moment of inertia I. The plates 208 have a radius r and are separated by a distance x. Between the plates 208, a plurality of springs 210 having a spring constant k and dampers 212 having a damping constant of C are provided. The model 200 may be subjected to different control inputs. For example, one set of control inputs may include rotations $\varphi_{y,0}$, $\varphi_{p,0}$, and a translation $x_0$. The dynamic response of the model 200 is recorded and can be employed for comparison against measured data. In a particularly useful embodiment, the dynamic response may be employed to predict the motion of the shape sensing enabled instrument 102. Predicted behavior can then be compared to optical characterization measurements to evaluate errors therein.

Noise models, e.g., employed in a Kalman filter are derived by translating optical characterization measurements of the shape sensing enabled instrument 102 into a disturbance term that is added to the dynamic model of the instrument 102. Such models can also account for measurement features specific to OSS. For example, since measurement errors increase towards the tip of the fiber, the influence of the noise can be predicted to be stronger for the mass-spring-damper systems that represent the tip of the catheter 202. These noise models can assume white noise processes with different variance levels as a function of position along the device, or more sophisticated models can account for the correlated nature of measurements from nearby locations along the device.

Figure 3:
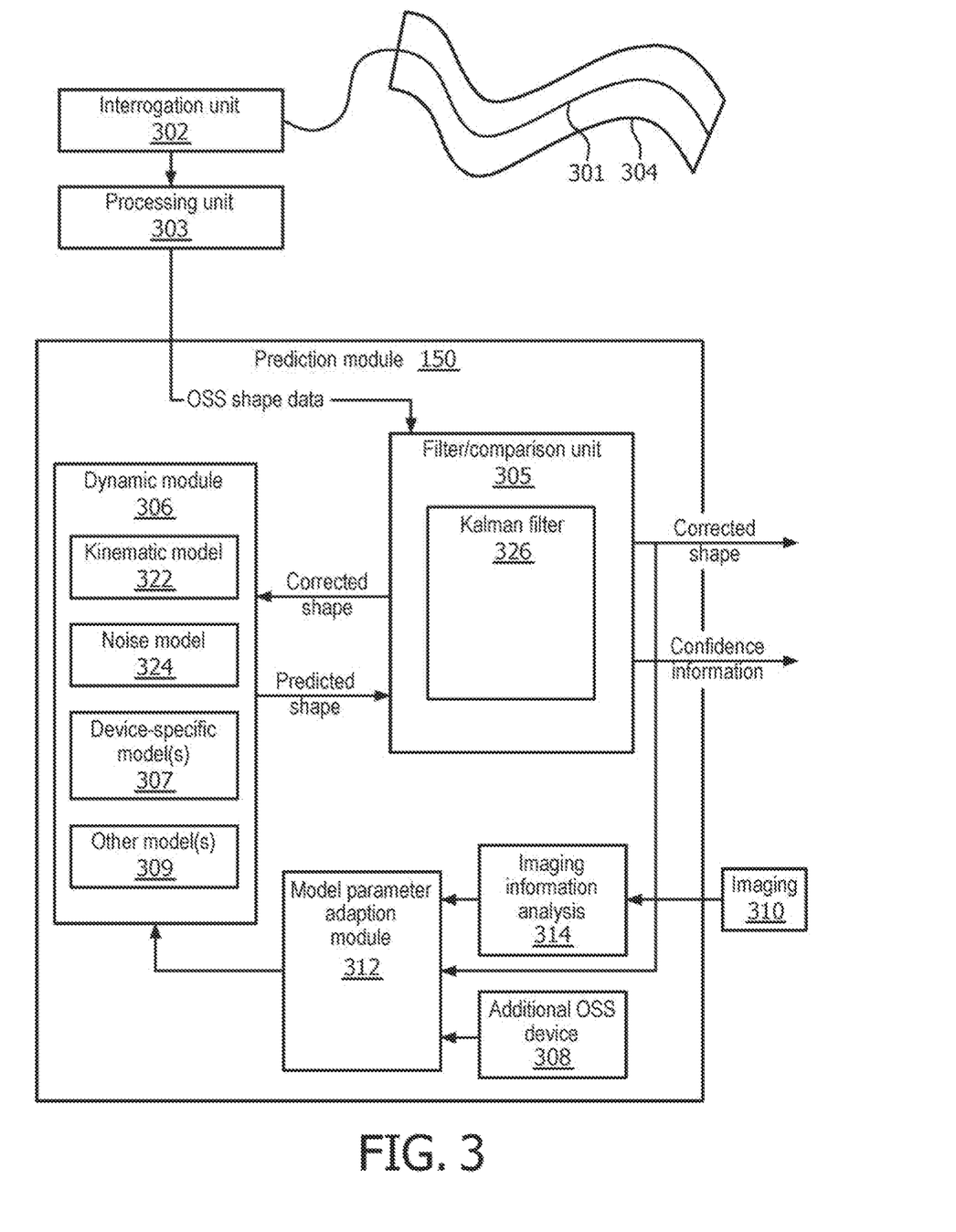
FIG. 3 is a block/flow diagram of a shape sensing system showing greater detail for a prediction module for improving accuracy and stability of shape data in accordance with another embodiment.
Figure 3A:
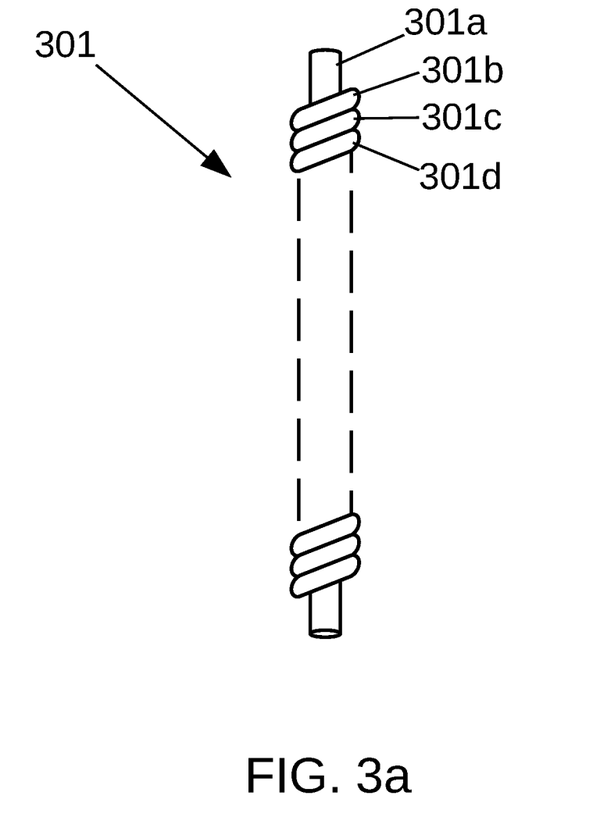
FIG. 3a illustrates a detail of the shape sensing multi-core fiber of FIG. 3.

Referring to FIG. 3, a prediction module 150 is shown in accordance with one illustrative embodiment. The prediction module 150 receives shape measurement data from a shape sensing enabled device 304 including, e.g., with reference to FIG. 3a, a shape sensing multi-core fiber 301 with a central core 301a and at least three outer cores 301b, 301c, 301d helically wound around the central core. The shape sensing enabled device 304 may include a catheter or similar supporting medical device in which the shape sensing multi-core fiber 301 is incorporated and which measures or tracks the movement of the fiber/device assembly.

An interrogation unit 302 delivers light to the shape sensing fiber 301 and detects the reflected signals from either intrinsic Rayleigh scattering or fiber Bragg gratings (FBGs) in an interferometric way. A processing unit 303 (and accompanying module 115, shown in FIG. 1) translates the measured reflection spectra into 3D shapes.

A filter or comparison module 305 combines a shape measurement with the prediction from a dynamic model 306 in a weighted average. The corrected shape is sent back to the dynamic model 306 to make a prediction for the next state of the device 304. The filter or comparison module 305 may include a Kalman filter/method 326, which is capable of determining a best source of data (e.g., measured or predicted) to decide on a best correction (weighting) for the shape data.

The corrected past data may be employed to compare to most likely configurations of the device 304 in accordance with the dynamic model 306. The dynamic model 306 may include a kinematic model 322, which models the physical attributed and motion of the device 304. The dynamic model 306 may include a noise model 324, which models expected noise so that this noise can be extracted out. The dynamic model 306 may include a device-specific kinematic or device-specific noise model 307. The noise model 307 may consider the type, shapes and use of the device 304 and better define noise sources specific to that device 304 and/or its particular application. Other models 309 may also be employed.

Once the most likely configuration is determined based on the past shape, a predicted shape is output for the device 304 for the current shape data. Because the device 304 may be kinematically modeled, its next configuration can be predicted based upon its current shape (or based on past shapes). This can be provided statistically as there are more likely configurations than others for devices 304 having a particular current shape. The predicted result is provided to the comparison or filter module 305, which compares the predicted result to the measured result to improve accuracy and reduced jitter. In one embodiment, erroneous data may also be determined.

The filter/comparison module 305 uses the Kalman filter 326 to get a more reliable shape and to possibly compute information about the reliability of the shape (e.g., confidence scores or information). This reliability information can then be used to decide whether to discard the shape or portion of the shape after the prediction by the model 322 and the measurement have been combined by the Kalman filter 326.

The filter/comparison module or unit 305 may output confidence information on the corrected shape. In one embodiment, a user may be able to select whether the data should be removed based on the confidence information. In another embodiment, the confidence information is employed to assist in automatically removing erroneous data. Predicted data from a past cycle may be compared to measured data from a current cycle to determine its value and reject it if it is unphysical or erroneous.

The dynamic model 306 returns a prediction on a future state of the shape sensing enabled device 304 based on its current state. The dynamic module 306 may include several models or sub-models, e.g., a noise model 307 may be included to compare noise profiles between a measured signal and a reference. Other models 309 may include a material response model, etc. The models 307, 309, etc. may provide instrument specific filtering, by deriving for each shape sensed instrument a noise or mechanical model from the optical characterization of the fiber integrated in that specific instrument.

Another OSS device or devices 308 may be included for obtaining shape data by a separate method. The device 308 may include a second OSS system, electromagnetic (EM) sensors, etc. In this way, collected data can be compared with the reference data from two or more sources. This can provide increased confidence in providing accurate measurement data and/or removing erroneous data. In addition or instead of device 308, an imaging device 310 (110, FIG. 1) may be employed to confirm the measurement data from the device 304. This can also provide increased confidence.

An imaging information analysis module 314 gathers information about the shape sensed instrument from auxiliary imaging equipment (e.g., from imaging device 310, which may include X-ray, ultrasound, etc.) and uses this information to adjust or correct the instrument specific model or filter parameters using a model parameter adaptation module 312. The model parameter adaptation module 312 may employ input from the imaging information analysis module 314, from the data of a second OSS device 308, corrected shape data obtained from the filter module 305, etc. These inputs to the model parameter adaptation module 312 may be employed to adjust and/or correct instrument specific model parameters or filter parameters in the dynamic model 306. An optimization of the instrument kinematic model 306 can take place post-assembly, after the manufacturing or calibration processes, pre-procedurally, or even updated adaptively intra-procedurally to allow for tuning of instrument tracking to adapt performance to different phases of the procedure itself.

The filter module 305 may receive OSS data from the device 304 and output filtered/corrected data to the kinematic model 306. The dynamic model 306 performs the comparisons with reference models and outputs a predicted shape. The predicted shape is processed by filter module 305 to provide corrected predicted shape data and associated confidence scores. Using predicted information, better estimates of useful shape data can be made by understanding likely shape sensing data, which can be compared to measured shape sensing data to determine its reliability, accuracy and stability. If the measured data coming in from the device 304 does not match the predicted data, the measured data becomes suspect and depending on the confidence score can be disregarded, partially disregarded or accepted.

The filter module 305 preferably includes a Kalman filter 326. The Kalman filter 326, also known as linear quadratic estimation (LQE), uses a series of measurements observed over time, containing noise (random variations) and other inaccuracies, and produces estimates of unknown variables that tend to be more precise than those based on a single measurement alone. The Kalman filter 326 of module 305 operates recursively on streams of noisy input data to produce a statistically optimal estimate of the underlying system state.

The Kalman filter 326 works in a two-step process. In a prediction step, the Kalman filter 326 produces estimates of the current state variables, along with their uncertainties. Once the outcome of the next measurement (necessarily corrupted with some amount of error, including random noise) is observed, these estimates are updated using a weighted average, with more weight being given to estimates with higher certainty. The weightings can be determined based upon the kinematics of the device 304 from the dynamic model 306. Because of the recursive nature, the Kalman filter 326 can run in real-time using only the present input measurements and the previously calculated state; no additional past information is required. The Kalman filter 326 of module 305 also yields a conditional probability estimate (e.g., Gaussian-distributed errors).

Extensions and generalizations may also be employed (e.g., the extended Kalman filter, the unscented Kalman filter, which works on nonlinear systems, etc.). An underlying model of the Kalman filter 326 is a Bayesian model similar to a hidden Markov model, but the state space of latent variables is continuous and where all latent and observed variables have Gaussian distributions. As such, based upon the filtering confidence (confidence information), scores can be generated for the filtered output (e.g., leading to corrected shapes).

The Kalman filter 326 employs the dynamic model 306 (e.g., physical laws of motion), known control inputs to that system, and multiple sequential OSS measurements to form an estimate of the system's varying quantities (its state) that is better than the estimate obtained by using any one measurement alone.

All measurements and calculations based on models are estimates to some degree. Noisy sensor data, approximations in the equations that describe how a system changes, and external factors that are not accounted for introduce some uncertainty about the inferred values for a system's state. The Kalman filter 326 of module 305 averages a prediction of a system's state with a new measurement using a weighted average. The purpose of the weights is that values with better (i.e., smaller) estimated uncertainty are "trusted" more. The weights are calculated from covariance, a measure of the estimated uncertainty of the prediction of the system's state. The result of the weighted average is a new state estimate that lies between the predicted and measured state, and has a better estimated uncertainty than either alone. This process is repeated every time step, with the new estimate and its covariance informing the prediction used in the following iteration. The Kalman filter 326 of module 305 works recursively and only needs the last "best guess", rather than the entire history, of a system's state to calculate a new state.

Kalman gain is a function of the relative certainty of the measurements and current state estimate, and can be "tuned" to achieve a particular performance. With a high gain, the filter places more weight on the measurements, and thus follows them more closely. With a low gain, the filter follows the model predictions more closely, smoothing out noise. At the extremes, a gain of one causes the filter of module 305 to ignore the state estimate entirely, while a gain of zero causes the measurements to be ignored.

When performing the calculations for the filter, the state estimate and covariances may be coded into matrices to handle the multiple dimensions involved in a single set of calculations. This permits representation of linear relationships between different state variables (such as position, rotation, etc.) in any of the transition models or covariances.

Figure 4:
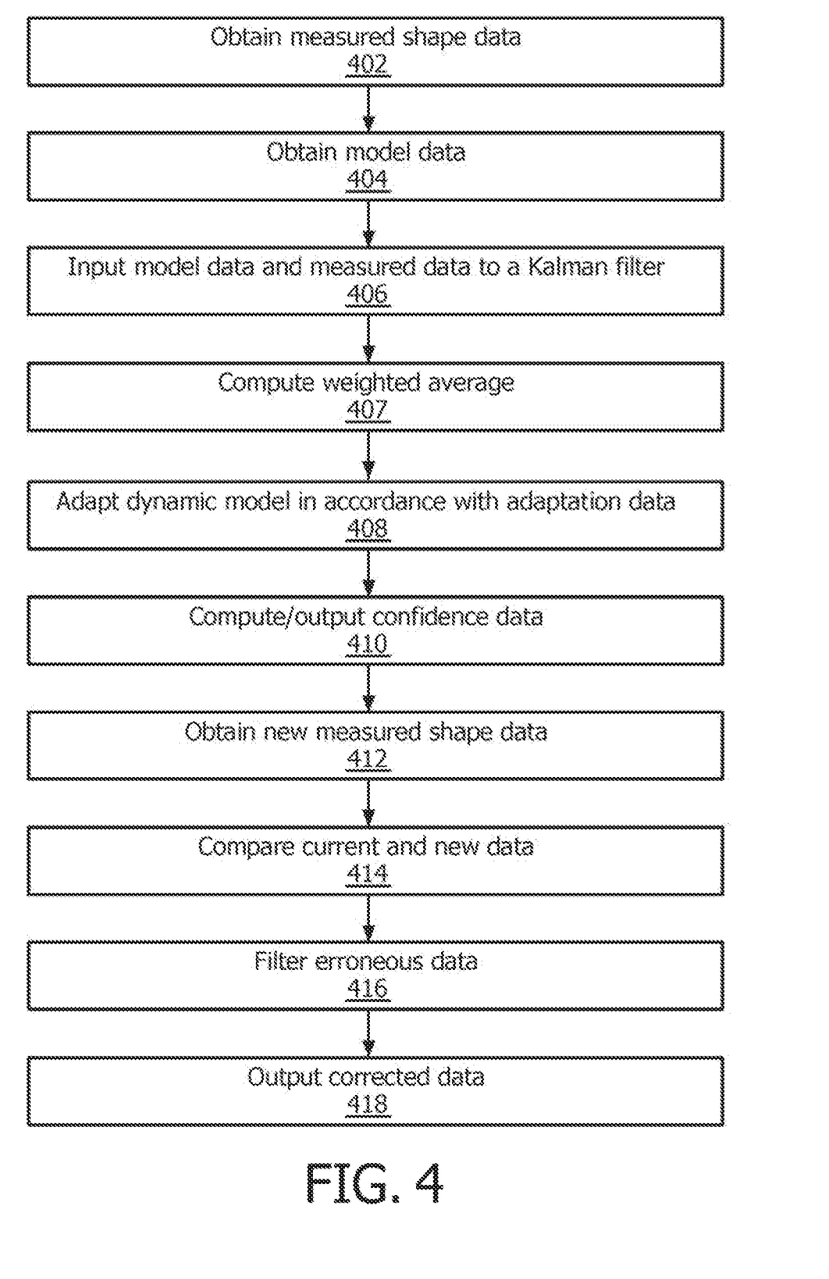
FIG. 4 is a flow diagram showing a method for improving accuracy and stability of shape sensing data for an optical shape-sensing system in accordance with an illustrative embodiment.

Referring to FIG. 4, a method for sensing a shape of a device is illustratively shown. In block 402, measured shape data is obtained from a shape sensing enabled device. The measured shape data may be obtained from optical fiber measurements of a shape sensing enabled medical instrument, e.g., a catheter or the like. In block 404, model data is obtained from a dynamic model of the shape sensing enabled device.

In block 406, the measured shape data and the model data are input to a Kalman filter, which is configured to predict new state data based on the measured shape data and a dynamic model of the shape sensing enabled device. The dynamic model may include a kinematic model (e.g., a mass-spring-damper model), a finite element model, an equation of equations, a noise model, a device-specific model, etc. In one embodiment, the predicted shape data employs a noise model, and in particular, a device-specific noise model for a given shape sensing enabled instrument. In block 407, a weighted average is computed between the measured shape data and the model data to predict new state data to improve the measured shape data.

In block 408, the dynamic model may be adapted in accordance with adaptation data. The adaptation data may be collected from one or more sources. These sources may include, e.g., an additional same type of shape sensing enabled device, a different type of shape sensing enabled device and imaging data collected for the shape sensing enabled device and newly measured shape data.

In block 410, confidence scores may also be computed for the new state data. In block 412, new measured shape data is obtained from the shape sensing enabled device. In block 414, the new measured shape data is compared against predicted new state data to evaluate the new measured shape data. In block 416, erroneous data may be filtered or corrected based upon confidence scores, comparison to the kinematic model, comparison with prior data, experience, etc. In block 418, corrected measurement shape data may be output.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for adaptive instrument kinematic model optimization for optical shape sensed instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A shape sensing system, comprising:
an elongated flexible medical instrument configured for insertion into an internal region of a subject, the medical instrument including one of a catheter, a guidewire, a probe, an endoscope, a robot or a balloon device, the medical instrument being outfitted with an optical fiber shape sensing device configured to output shape sensing measurements indicative of measured 3D shapes of the elongated flexible medical instrument as the elongated flexible medical instrument flexes and changes shape during insertion, the optical fiber shape sensing device including a shape sensing multi-core fiber with a central core and at least three outer cores helically wound around the central core;
a display configured to display an image of the internal region of the subject;
a processor coupled to a memory storage device;
a predictive model module stored in the memory storage device and configured to receive the measured 3D shapes of the elongated flexible medical instrument during insertion and predicted 3D shapes of the elongated flexible medical instrument based upon a current measured 3D shape of the elongated flexible medical instrument, the predictive model module including:
a Kalman filter;
at least one kinematic model including mass-spring-damper model of the elongated flexible medical instrument employing mechanical and material parameters of the elongated flexible medical instrument which provides the predicted 3D shapes of the elongated flexible medical instrument to the Kalman filter, the Kalman filter weightingly combines the current measured 3D shape of the elongated flexible medical instrument and one or more of the predicted 3D shapes to generate an improved 3D shape of the elongated flexible medical instrument;
a comparison module configured to generate confidence scores for the measured 3D shape of the elongated flexible medical instrument, the confidence scores being used to adjust the weighting with which the measured 3D shape and the predicted next 3D shapes are combined; and
wherein the processor is configured to control the display to display the image of the internal region overlaid with the improved 3D shape of the elongated flexible medical instrument.

2. The system as recited in claim 1, wherein the mass-spring-damper model is based on stiffness, material density, and geometry of the elongated flexible medical instrument.

3. The system as recited in claim 1, wherein the at least one kinematic model also includes a device-specific noise model for a given shape sensing enabled device indicative of noise which affects an accuracy of the measured 3D shapes.

4. The system as recited in claim 1, further comprising a model parameter adaptation module configured to update the at least one kinematic model in accordance with shapes of the elongated flexible medical instrument from another source.

5. The system as recited in claim 1, wherein the at least one kinematic model includes 3D shape data stored in a library of 3D shapes from previously acquired training cases including different phases of interventional procedures.

6. The system as recited in claim 1, wherein the predictive model further includes a dynamic model of physical laws of motion to estimate spatio-temporally-varying quantities.

7. A method for determining a 3D shape of an elongated, flexible shape sensing enabled interventional medical device, the method comprising during performance of an interventional procedure on a subject using the elongated, flexible shape sensing enabled interventional medical device:
(a) measuring the 3D shape of the elongated, flexible shape sensing enabled interventional medical device along its length and determining a confidence score regarding an accuracy of the measured 3D shape,
(b) obtaining a dynamic model for at least one modeled 3D shape of the elongated, flexible shape sensing enabled interventional medical device wherein the dynamic model models shape based on mechanical and material parameters of the interventional medical device, and a confidence score for each modeled 3D shape;

(c) inputting the measured 3D shape and the at least one modeled 3D shape into a Kalman filter;

(d) computing a weighted average in accordance with the confidence score of the measured 3D shape and the at least one predicted 3D shape to predict new state data of an improved 3D shape of the elongated, flexible shape sensing enabled interventional medical device;

(e) overlaying a rendering of the improved measured 3D shape of the elongated, flexible shape sensing enabled interventional medical device on an internal image of the subject; and (f) repeating steps (a)-(e) as the elongated, flexible shape sensing enabled interventional medical device moves longitudinally in the subject, wherein computing the weighted average includes additional dynamic models, and wherein the weighting is adjusted in accordance with the confidence score.

8. The method as recited in claim 7, further including:

(g) receiving another source 3D shape of the elongated, flexible shape sensing enabled interventional medical device from another source; and (h) adjusting the dynamic model data and the confidence value based on the another source 3D shape.

9. The method as recited in claim 7, wherein the dynamic model is based on at least stiffness, material density, and geometry of the interventional medical device.

10. The method as recited in claim 7, wherein the dynamic model includes a mass-spring-damper model.

11. A shape sensing system comprising:

a memory storing dynamic model data for a plurality of elongated, flexible shape sensing enabled interventional devices configured for being inserted in an internal region of a subject, the dynamic model data being based on physical and mechanical properties of the elongated, flexible shape sensing enabled interventional devices;

a selected one of the elongated, flexible shape sensing enabled interventional medical devices;

a display device; and one or more processors configured to:
(a) measure the 3D shape of the selected elongated, flexible shape sensing enabled interventional medical device along its length and determining a confidence score regarding an accuracy of the measured 3D shape;
(b) retrieve the dynamic model data for the selected elongated, flexible shape sensing enabled interventional medical device and modeling the 3D shape for the selected elongated, flexible shape sensing enabled interventional medical device;
(c) input the measured 3D shape and the at least one modeled 3D shape of the selected elongated, flexible shape sensing enabled interventional medical device into a Kalman filter;
(d) compute a weighted average in accordance with the confidence score of the measured 3D shape and the modeled 3D shape to predict new state data of an improved 3D shape of the selected elongated, flexible shape sensing enabled interventional medical device;
(e) overlay a rendering of the improved measured 3D shape of the elongated, flexible shape sensing enabled interventional medical device on an internal image of the subject; and
(f) repeat steps (a)-(e) during insertion of the elongated, flexible shape sensing enabled interventional medical device in the internal region of the subject,
wherein the memory further stores additional dynamic models and the one or more processors are further configured to compute the weighted average including the additional dynamic models, and
wherein the one or more processors are further configured to adjust the weighting in accordance with the confidence score.

12. The system as recited in claim 11, wherein the dynamic model data is based on at least stiffness, material density, and geometry of the interventional medical device.

13. The system as recited in claim 11, wherein the dynamic model includes a mass-spring-damper model.

* * * * *